United States Patent [19]

Guttman

[11] Patent Number: 5,213,669
[45] Date of Patent: May 25, 1993

[54] CAPILLARY COLUMN CONTAINING A DYNAMICALLY CROSS-LINKED COMPOSITION AND METHOD OF USE

[75] Inventor: Andras Guttman, Palo Alto, Calif.

[73] Assignee: Beckman Instruments, Inc., Fullerton, Calif.

[21] Appl. No.: 829,638

[22] Filed: Jan. 31, 1992

[51] Int. Cl.$^5$ ............... G01N 27/26; B01D 57/02
[52] U.S. Cl. .................... 204/180.1; 204/299 R
[58] Field of Search .................. 204/180.1, 299 R

[56] References Cited

U.S. PATENT DOCUMENTS 4,997,537  3/1991  Karger .................. 204/299 R

FOREIGN PATENT DOCUMENTS 90301508.9  8/1991  European Pat. Off.
WO9111709   8/1991  PCT Int'l Appl.

OTHER PUBLICATIONS

Bode, H-J. "SDA-Polyethyleneglycol Electrophoresis: A Possible Alternative to SDS-Polyacrylamide Gel Electrophoresis" 65/1:56-58 *FEBS* Letters (1976).

Widhalm, A. et al., "Capillary Zone Electrophoresis with a linear non-crosslinked polyacrylamide gel: Separation of proteins according to molecular mass," *J. Chron.* 549: 446-451 (1991).

Tsuji, K. "High-Performance Capillary Electrophoresis of Proteins. Sodium dodecyl sulphate-polyacrylamide gel-filled capillary column for the determination of recombinant biotechnology-derived proteins." *J. Chron.* 550: 823-830 (1991).

Primary Examiner—Donald R. Valentine
Assistant Examiner—John S. Starsiak, Jr.
Attorney, Agent, or Firm—William H. May; P. R Harder; Richard P. Burgoon, Jr.

[57] ABSTRACT

Disclosed herein is a capillary column containing a dynamically cross-linked composition and method of use. In a particularly preferred embodiment, the dynamically cross-linked composition comprises: 1.0% polyethylene oxide; 1.0% polyethylene glycol; 1.0% ethylene glycol; 100 mM TRIS-CHES buffer; and 0.1% sodium dodecyl sulphate, where the pH of the composition is between about 8.0 and about 9.0 and the viscosity of the composition is less than about 500 centipoise. The disclosed compositions can be used for the analysis of surfactant:proteinaceous material complexes and the generation of calibration curves over an extensive range of molecular weights, using capillary electrophoretic techniques. The disclosed compositions are particularly suited for capillary electrophoretic systems having UV-based detection.

39 Claims, 3 Drawing Sheets

CAPILLARY COLUMN CONTAINING A DYNAMICALLY CROSS-LINKED COMPOSITION AND METHOD OF USE

FIELD OF THE INVENTION

The present invention is directed to the analysis of samples in general and in particular to the analysis of proteinaceous materials using capillary electrophoretic techniques. In a particular embodiment, the invention is directed to a capillary column containing a dynamically cross-linked composition useful in the analysis of surfactant:proteinaceous material complexes by capillary electrophoresis.

BACKGROUND OF THE INVENTION

Capillary gel electrophoresis is one of the most widely used separation techniques in the biologically-related sciences. Molecular species such as proteins, peptides, nucleic acids, and oligonucleotides are separated by causing the species to migrate in a buffer solution under the influence of an electric field. The buffer solution normally is used in conjunction with a low to moderate concentration of an appropriate gelling agent such as agarose or polyacrylamide to minimize the occurrence of mixing of the species being separated. Two primary separating mechanisms exist: a) separations based on differences in the effective charge of the species; and b) separations based on molecular size.

The first of these mechanisms is generally limited to low or moderate molecular weight materials, such as small oligonucleotides (about 1 to about 50 nucleotides in length). This is because there is typically an insignificant difference between the effective charges of high molecular weight materials, making the task of separation difficult or impossible.

Separations based on molecular size are generally referred to as molecular "sieving". Molecular sieving utilizes gel matrices having controlled pore sizes as the separating medium. The separation results from the relative abilities of the different size molecular species to penetrate through the gel matrix; smaller molecules move more quickly than larger molecules through a gel of a given pore size.

Medium-to-high molecular weight oligonucleotides (greater than about 50 nucleotides in lenght), polypeptides, and proteins are commonly separated by molecular sieving electrophoresis. Proteins are heteropolyelectrolitic (i.e. an approximate equivalent number of negative charged and positive charged moieties where the overall molecule has a net neutral charge). As such, proteins become charged molecules as they transit a charged capillay column. Accordingly, in order to separate proteinaceous materials based upon the size of the molecules, these materials must have the same effective charge to mass ratio as they traverse the capillary column.

Achieving the same effective charge to mass ratio is commonly accomplished by treating the proteinaceous materials with a surfactant, such as sodium dodecyl sulphate ("SDS"), and utilizing a polyacrylamide gel material as the seiving medium. Such a procedure is referred to as sodium dodecyl sulphate polyacrylamide gel electrophoresis ("SDS-PAGE"). See, for example, *Gel Electrophoresis of Proteins: A Practiced Approach* (Second Ed). B. D. Harnes & D. Rickwood, Eds. IRL Press, Oxford University Press, 1990. See also, *New Directions in Electrochoretic Methods.* T. W. Jorgenson & M. Phillips, Eds. published by American Chemical Society, Washington, D.C. 1987. Both of these references are incorporated fully herein by reference.

A surfactant, such as SDS, comprises a hydrophobic (water-hating) "tail" and a hydrophillic (water-loving) "head." Thus, a surfactant interacts with a protein species via hydrophobic interactions between the hydrophobic "tail" of the surfactant and the protein species. Upon ionization, the hydrophillic "head" of the surfactant molecules surrounding the protein species become negatively charged, positively charged, or remain neutral; upon ionization, SDS becomes negatively charged. Accordingly, an SDS:protein complex has a uniform charge distribution, and such a complex can then be separated based upon size relative to the pore-size distribution throughout the gel matrix.

Commercially available capillary electrophoresis instruments the P/ACE TM high performance capillary electrophoresis system (Beckman Instruments, Inc., Fullerton, Calif., U.S.A.), utilize a detection system based upon ultra-violet ("UV") light absorption. While UV detection of SDS-protein complexes in polyacrylamide filled capillaries is possible, such detection is limited to a specific wavelength detection of about 250 nm and higher. This is because of the high UV absorbance associated with both crosslinked and uncrosslinked polyacrylamide gels.

Such dection limitations are a distinct disadvantage particularly with respect to the analysis of proteins. This is because proteins absorb UV light very strongly at 214 nm, due to peptide bonds within proteins. Thus, UV detection of proteins should be conducted at about 214 nm. However, because of the 250 nm and higher detection limitations created by the use of polyacrylamide gels, the sensitivity and selectivity of UV detection of proteinaceous materials using polyacrylamide-based gel systems is limited.

Accordingly, UV detection of surfactant:proteinaceous materials would be greatly improved if on-column detection was conducted at lower UV wavelengths. This, in light of the foregoing, requires molecular sieving materials that do not suffer the drawbacks of polyacrylamide gels.

SUMMARY OF THE INVENTION

Disclosed herein are capillary columns containing dynamically cross-linked compositions and which are applicable to the analysis of surfactant:proteinaceous material complexes by capillary electrophoresis. In a preferred embodiment, the dynamically cross-linked compositions comprise between about 0.01% and about 1.5% polyethylene oxide; between about 0.0% and less than about 2.00% polyethylene glycol; between about 0.0% and about 2.0% of a surfactant; between about 0.0% and about 99.0% of a polyol; and between about 0.0M and 1.0M of a pH buffer, where the pH of the composition is between about 2.0 and about 10.0. Preferably, the viscosity of the dynamically cross-linked composition is less than about 4,000 centipoise, more preferably less than about 500 centipoise, and preferably about 150 centipoise. The compositions are particularly useful in the analysis of SDS-protein complexes using UV detection-based capillary electrophoretic systems, although other detection systems based upon, e.g., radioactive or fluorescence detection, are equally applicable. The capillary columns can be either untreated or coated with a conventional coating material.

BRIEF DESCRIPTION OF THE DRAWINGS

The following drawings are presented for the purpose of reference in conjunction with the Detailed Description of Preferred Embodiments of the Invention.

DETAILED DESCRIPTION OF PREFERRED EMBODIMENTS

Figure 1:
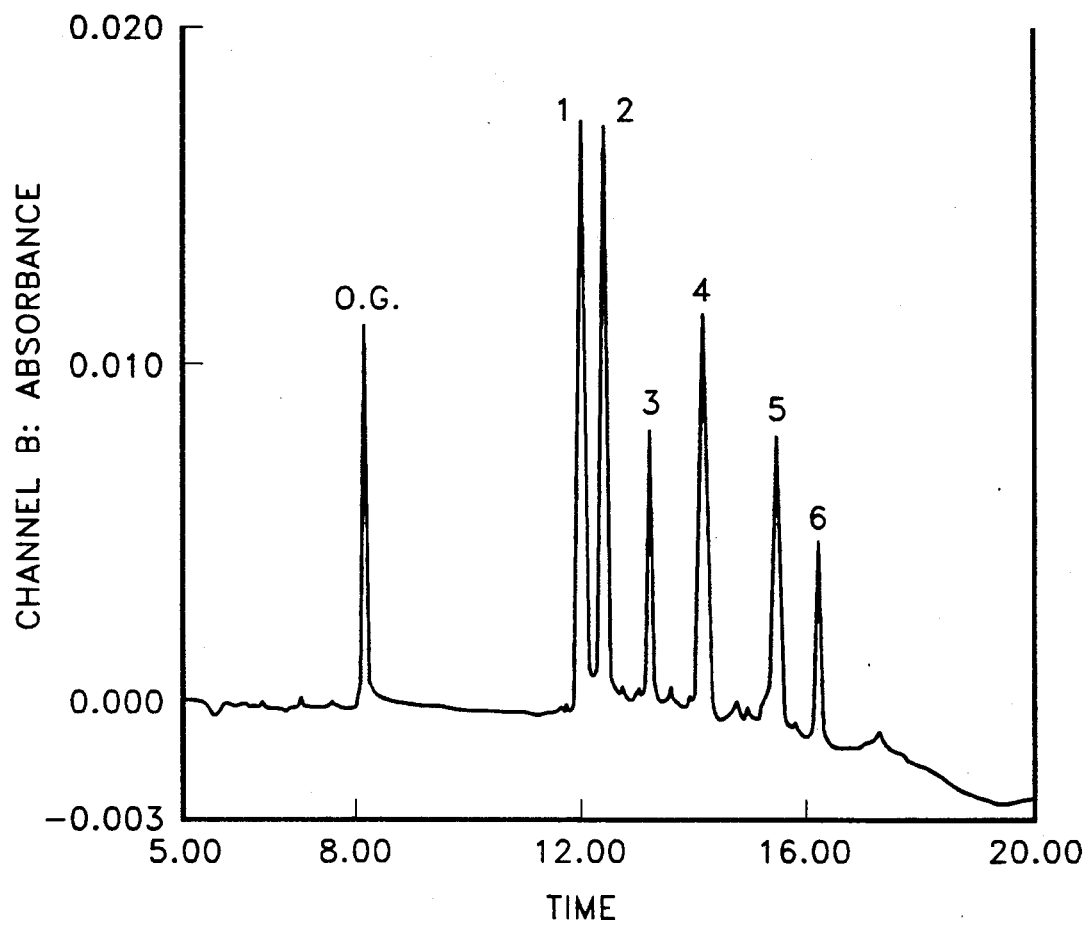
FIG. 1 is an electropherogram of the separation of low molecular weight SDS-protein standard mixture using a 1.0%PEO/1.0%PEG dynamically cross-linked composition.

Disclosed herein are capillary columns containing dynamically cross-linked compositions for use in, most preferably, the analysis of surfactant:proteinaceous material complexes using capillary electrophoretic techniques.

As used herein, the phrase "dynamically cross-linked composition" means a gel-like solution having a three-dimensional network of polymer chains held together by hydrogen bonding and dispersed in a liquid phase. The dynamically cross-linked composition is a viscous liquid having a sufficient structure for a degree of rigidity which allows for, inter alia. molecular sieving based upon the size of the materials to be separated. Preferably, the viscosity of the composition is less than about 4,000 centipoise, and more preferably less than about 500 centipoise. When the composition does not include PEG, it is a linear, as opposed to cross-linked, composition. PEG is preferably added to the composition to dynamically cross-link the PEO. Accordingly, "dynamically cross-linked composition," as that phrase is used herein, includes linear compositions such as compositions not including PEG as described above.

As used herein, the term "capillary column" means a capillary comprising an interior cavity defined by a wall with an inner surface, where the internal diameter range of the capillary is between about 2 $\mu$m and 2000 $\mu$m. If the detection system of the capillary electrophoretic system is based upon UV absorbance, then the capillary is preferably made of a UV transparent material, such as, for example, glass or fused silica, with fused silica being most preferred. If the detection system of the capillary electrophoretic system is based upon, e.g. radioactive detection of fluorescence detection, then the capillary is preferably made of a material conducive to such systems. Alumina, beryillium, TEFLON TM - coated materials, glass and fused silica are exemplary materials. The capillary column should be capable of withstanding a wide range of applied electrophoretic fields of between about 10 volts per centimeter ("V/cm"), up to about 1000V/cm. The capillary column may be coated on the outside (using, e.g., a polyamide material) for ease of handling. The inner wall of the capillary may be untreated or coated with a coating material which is available or known to those in the art. An example of a preferred coating material is disclosed in U.S. Pat. No. 5,098,539, which is incorporated fully herein by reference. Preferably, the internal diameter of the capillary column is between about 2 $\mu$m and 2000 $\mu$m and most preferably about 100 $\mu$m.

The term "UV transparent" as used herein, means having negligible absorbance throughout the UV wavelength range of between about 195 nm and about 350 nm.

As used herein, the term "surfactant" is a substance having hydrophobic and hydrophillic properties, and exhibiting either a negative charge, a positive charge or neutral charge upon ionization. The hydrophobic portion of the surfactant is capable of interacting with a proteinaceous material via hydrophobic interactions such that the material is surrounded by the hydrophilic portion of the surfactant. Representative anionic surfactants include, for example, sodium-dodecyl sulphate ("SDS"), decyl-sulphate, and deoxycholate. Representative cationic surfactants include, for example cetyl-trimethylammonium bromide ("CTAB") and cetylpyridinium chloride ("CPC"). Representative non-ionic surfactants include, for example, polyoxyethylene ethers such as Triton X 100 TM and Triton DF-16 TM, and polyoxyethylenesorbitans such as BRIJ-35 TM, the TWEEN TM surfactants, and LUBROL W TM. All of the foregoing trademark-designated surfactants are available from Sigma Chemical Co., St Louis, Mo. Of the surfactants, anionic surfactants are preferred when used in conjunction with untreated fused silica columns. Most preferably, the surfactant is SDS.

As used herein, the term "proteinaceous material" means, proteins (both natural and those derived via recombinant nucleic acid technology), peptides, polypeptides, nucleic acids and oligonucleotides. It is to be understood that while the disclosed dynamically cross-linked composition finds particular applicability in the analysis of proteinaceous materials, and in particular proteins, the disclosure is not limited to such materials. Thus, the disclosed dynamically cross-linked composition can be utilized for the analysis of other materials capable of being analyzed by capillary electrophoretic techniques. Because proteinaceous materials as defined herein can be charged upon ionization, it is to be understood that the dynamically cross-linked composition need not incorporate a surfactant therein. For example, deoxyribonucleic acid ("DNA") molecules have the same charge-to-mass ratio; therefore, a surfactant is not required to achieve this result. However, it is preferred that the composition include a surfactant for the analysis of proteinaceous materials.

The dynamically cross-linked composition comprises the following materials: i) between about 0.01% and about 1.5% polyethylene oxide ("PEO"); ii) between about 0.0% and less than about 2.0% polyethylene glycol ("PEG"); iii) between about 0.0% and about 2.0% of a surfactant; iv) between about 0.0% and about 99% of a polyol; and v) between about 0.0M and about 1.0M of a pH buffer, where the composition has a pH of between about 2.0 and about 10.0, and the viscosity of the composition is less than about 4,000 centipoise.

In a particulalry preferred embodiment, the dynamically cross-linked composition comprises about 1.0% PEO; about 1.0% PEG; about 0.1% of the same surfactant used in the formation of the surfactant:proteinaceous material complex; and 100 mM of a pH buffer, where the composition has a pH of between about 8.0 and about 9.0, and a viscosity of less than about 500 centipoise.

Uncoated, or untreated, capillary columns can be utilized in conjunction with the compositions. When uncoated capillary columns are used, the dynamically cross-linked composition further comprises between about 0.01% and about 99.00% of a polyol. The polyol, in effect, circulates throughout the polymer to "coat" the locations on the inner wall of the capillary which are not covered by the dynamically cross-linked composition. Representative polyols include, but are not limited to, ethylene glycol and glycerol. A preferred polyol is ethylene glycol. Most preferably the composition comprises about 1.0% of ethylene glycol. It is to be understood that the composition can (and preferably does) comprise polyol even when used in conjunction with coated capillary columns.

When the detection system of the capillary electrophoretic system is based upon UV absorbance, the pH buffer should be UV transparent. Exemplary UV transparent buffers include, for example, the so-called "Good" buffers (see Good, N. E. et al "Hydrogen Ion Buffers for Biological Research" *Biochemistry* 5/2: 467-477 (1966) which is incorporated herein by reference). The Good buffers can be described as being zwitterionic buffers covering the range of $pK_a$ from 6.15 to 8.75, and include 2-(N-morpholine) ethanesulfonic acid ("MES"), N-(2-acetamido) iminodiacetic acid ("ADA"), piperazine. N,N'-bis(2-ethanesulfonic acid ("PIPES"), n-(2-acetamido)-2-aminoethanesulfonic acid ("ACES"), (2-aminoethyl) trimethyl-ammonium chloride hydrochloride ("Cholamine"), N,N-bis(2-hydroxy-ethyl) 2-aminoethane sulfonic acid ("TES"),N-2-hydroxy-ethylpiperazine-N'-2-ethanesulfonic acid ("HEPES"), tris-hydroxymethyl amino methane ("TRIS"), N-tris(hydroxyl-methyl)methylglycine ("Tricine"), N,N-bis(2-hydroxyethyl)-glycine ("Bicine"), 2-(N-cyclohexylamino) ethane-sulfonic acid ("CHES"), and mixtures of the foregoing. A particularly preferred pH buffer for UV detection purposes is TRIS-CHES.

While the foregoing buffers are preferred for use in conjunction with UV detection, it is to be understood that such buffers can also be utilized with, e.g., radioactive detection or fluorescent detection instruments. Additionally, when UV detection is not utilized, buffers that include constituents having aromatic rings or peptide bonds can be utilized as the pH buffer. TRIS-histidine is an example of such a buffer.

The pH of the buffer is principally selected with respect to the type of surfactant utilized. For cationic surfactants, the pH of the buffer should be in the acidic range (i.e. between about 2.0 and 5.0); for anionic surfactants, the pH of the buffer should be in the alkaline range (i.e. between about 8.0 and 10.0); for nonionic surfactants, the pH of the buffer is between about 5.0 and 8.0. With respect to the preferred SDS surfactant, a most preferred pH is about 8.8.

For UV detection-based analysis of proteinaceous materials using untreated capillary columns, a particularly preferred embodiment of the dynamically cross-linked composition comprises about 1.0% PEO; about 1.0% PEG; about 0.1% SDS; about 1.0% ethylene glycol; and about 100 mM TRIS-CHES buffer, pH 8.8, and a viscosity of less than about 500 centipoise.

Capillary electrophoresis using the dynamically cross-linked composition disclosed above includes the steps of introducing an aliquot of a sample containing constituents to be separated into the column of the invention, applying an electric field of at least about 10 V/cm to the column, allowing a current of between about 1.0 to about 100 microampers($\mu$A) to pass through the column, and detecting the constituents of the sample as they migrate past an on-line detector. Introduction of the samples can be accomplished by the electrokinetic injection method or pressure injection; preferably, pressure injection is utilized. The electric field may be a continuous or pulsed electric field; those skilled in the art will appreciate the distinction between these types of fields. Preferably, a continuous electric field is utilized.

The capillary "running buffer" is dependent principally on the detection system. For UV detection, the running buffer should be UV transparent. Preferably, the running buffer is the same buffer utilized in the dynamically cross-linked composition. When the composition does not include a pH buffer, the running buffer is selected based upon the detection system, as indicated above. Accordingly, the pH buffers disclosed above can be utilized for the running buffer.

The dynamically cross-linked composition containing capillary columns are particularly suited for the analysis of proteinaceous materials over approximately 50 to 100 runs. As noted, the capillary column can be either coated or untreated. With respect to untreated columns, a deactivation solution should be passed through the capillary after approximately every 10 analytical runs. As used herein, the term "deactivation solution" is a solution which deactivates the surface of the untreated capillary column. For example, with fused silica, the SiO groups which occupy the inner surface of the capillary wall during electrophoresis should be converted to SiOH groups via the deactivation solution. A most preferred deactivation solution is 1M HCl.

The analysis of proteinaceous materials can be made at UV wavelengths of 214 nm using the disclosed composition. This is a distinct advantage over polyacrylamide gels. Additionally, the disclosed dynamically cross-linked polymer can be used for quantitative analysis of, e.g., proteinaceous materials over large molecular weight ranges. As those in the art appreciate, such calibration plots for polyacrylamide gels is quite difficult to achieve, thus heretofore making quantative analysis evasive.

The following examples are presented for illustrative purposes only and are not intended, nor should they be construed to be, a limitation on the foregoing disclosure or the claims to follow.

EXAMPLES

Capillary electrophoresis of samples described in the following Examples was performed on a Beckman Instruments, Inc. PACE TM high performance capillary electrophoresis system. This system contains built-in 200, 214, 254, 260, 280 and 415 nm narrow-band filters for on-line detection. The detection window was located approximately 7.0 cm from the column outlet and 40 cm from the column inlet.

Samples were placed on the inlet tray of the above-referenced capillary electrophoresis system. Samples were automatically injected into the dynamically cross-linked polymer capillary column by utilizing the pressure injection mode for 1-90 seconds.

Capillary columns, coated in accordance with the disclosure of U.S. Pat. No. 5,098,539 had a column length of 47 cm, an effective column length of 40 cm, and an internal diameter of 100 $\mu$m. Electric field strength was 300 V/cm (14.1 KV for 47 cm); current utilized was 25-30 $\mu$A.

EXAMPLE I

Material Preparation

A. Running Buffer Solution

A 0.5M TRIS-CHES buffer (pH 8.8) was prepared by dissolving 12.1 g TRIS (ICN Biochemicals, Irvine, Calif.; Product No. 819620) in 100 ml deionized water. Solid CHES (ICN, Product No. 101434) was added with continuous stirring until a pH of 8.8 was achieved. A final volume of 200 ml was achieved using deionized water.

B. Model Protein Sample Preparation

A 0.3M TRIS sample buffer was adjusted with 1:1 HCl to pH 6.6, followed by addition of 10% SDS thereto, as follows. 36.3 g TRIS was dissolved in 500 ml deionized water, followed by addition of 1:1 diluted HCl (VWR, San Francisco, Calif., Product No. VW3110-3) with continuous stirring and pH monitoring until a pH of 6.6 was achieved. 100 g SDS (ICN, Product No. 811034) was added with continuous stirring and a final volume of 1000 ml was achieved using deionized water.

Model Protein SDS-protein standards were as follows:
1) Bio-Rad Labs, Richmond, Calif., Catalogue No. 161-0303 (molecular weight range of 14,000–97,000 Daltons:Lysozyme; Soybean trypsin inhibitor; Carbonic anhydrase; Ovalbumin; Bovine Serum albumin; Phosphorylase b.); and
2) Bio-Rad Labs, Catalogue No. 161-0304 (molecular weight upper limit of 200,000 Daltons: Ovalbumin; Bovine Serum albumin; Phosphorylase b; Beta-galactosidase; Myosin).

Orange G ™ dye (7-hydroxy-8-phenylazo-1,3-naphthalenedisulfonic acid; Sigma Chemical Corp., St. Louis, Mo. Product No. 03756) was utilized as an internal standard. A 0.1% solution, in deionized water, was utilized for the Examples.

Protein disulfide linkages were broken using 2-mercaptoethanol (ICN, Product No. 190242). As those skilled in the art appreciate, in the presence of a surfactant and a reducing agent, most multichain proteins will bind the surfactant to a constant value and the disulfide bonds will be broken by the reducing agent. Thus, the secondary structure of the protein will be lost and the surfactant-protein complex is assumed to adopt a random coil confirmation. Accordingly, proteins treated in this manner have a uniform shape and identical mass to charge ratios. Thus, it should be appreciated that any reducing agent is applicable, such as, for example, dithiothreitol, (DTT) and mercaptoethanol.

Samples were prepared by admixing 0.1 to 0.2 mg of the Model Proteins (i.e. 20 μl of the Bio Rad materials), 40μl of the sample buffer; 10 μl of the Orange G solution; and 5 μl of 2-mercaptoethanol. A final solution volume of 125 μl was achieved using deionized water. This final mixture was boiled in a water bath (100° C.) for 15 min. in a closed microcentrifuge vial, then cooled on ice water for 2 min. before introduction into the capillary column.

C. Dynamically Cross-Linked Composition 10 g of PEO (MW 900,000; Aldrich Chemical Co., Milwaukee, Wis., Product No. 18,945-6) and 10 g PEG (mw 35,000; Fluka, Ronkonkoma, N.Y., Product No. 81310) were mixed with 10 ml ethylene glycol (VWR, Product No. EM-EX0564-1) and 50 ml deionized water for 10 min. in a 1.2 liter wide-neck flask. Thereafter, 700 ml of deionized water was added thereto, followed by stirring with a magnetic bar at 50° C. for three hours. After this, 200 ml of Running Buffer was added thereto, followed by stirring for one hour. 10 ml of 10% SDS (1.0 g SDS completely dissolved in 10 ml deionized water) was then added, followed by addition of deionized water to achieve a final volume of 1000 ml, and overnight stirring at room temperature. Prior to use, the dynamically cross-linked composition was sonicated for 5 min. to remove air bubbles.

The viscosity of the dynamically cross-linked composition was determined using an ELV-8 ™ viscometer, Col-Parmer, Inc., Chicago, Ill., using 100 ml of the composition. Viscosity was determined to be 150 centipoise at 25° C. relative to equal volumes of distilled water (20 centipoise) and glycerol (1100 centipoise) measured at the same temperature.

EXAMPLE II

Analysis of Low Molecular Weight SDS-Protein Standard Mixture

Excellent separation and specificity was achieved in less than 20 minutes for the analysis of the low molecular weight standards under the parameters set forth above. FIG. 1 provides the electropherogram results of such analysis, where "O.G." is the Orange G internal standard; "1" is Lysozyme "2" is Soybean trypsin inhibitor; "3" is Carbonic anhydrase; "4" is Ovalbumin; "5" is Bovine serum albumin; and "6" is Phosphorylase b.

EXAMPLE III

Analysis of High Molecular Weight SDS-Protein Standard Mixture

Figure 2:
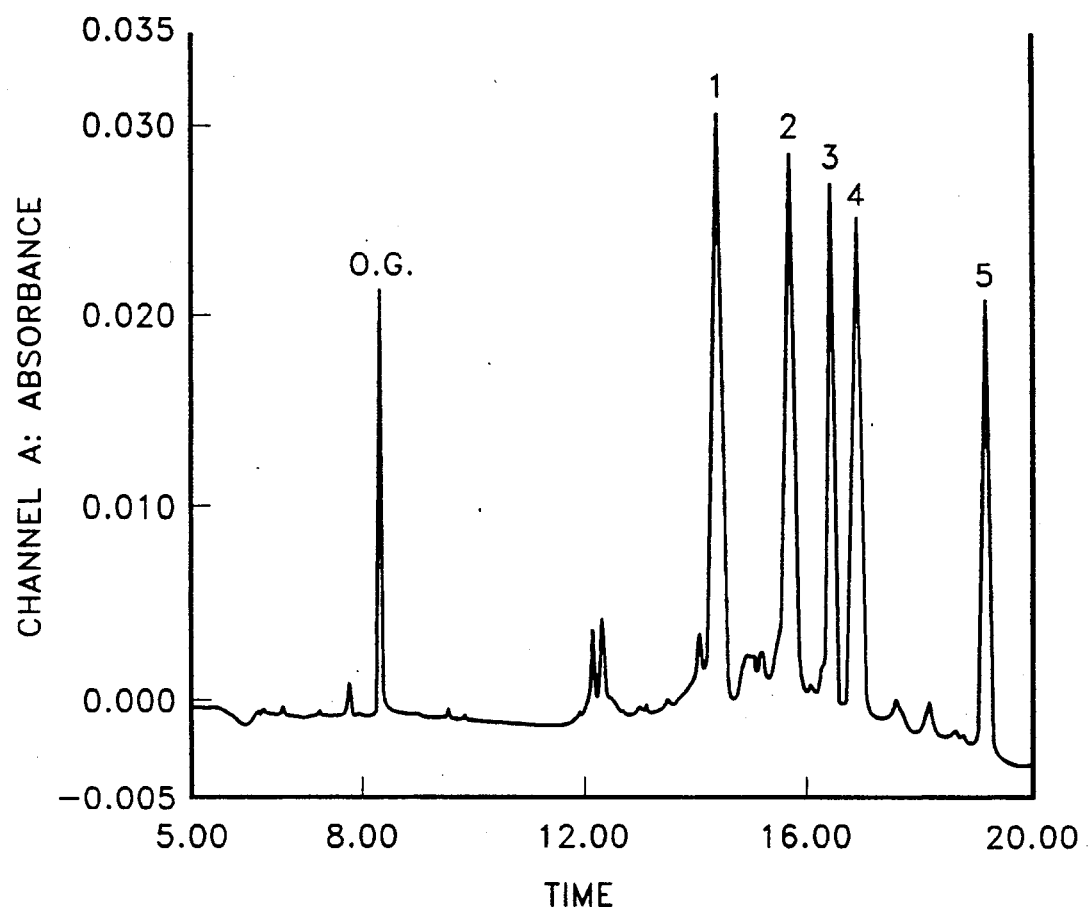
FIG. 2 is an electropherogram of the separation of high molecular weight SDS-protein standard mixture using the dynamically cross-linked composition of FIG. 1.

Excellent separation and specificity was achieved in less than 20 minutes for the analysis of high molecular weight standards under the parameters set forth above. FIG. 2 provides the electropherogram results of such analysis where OG is as defined in Example II; "1" is Ovalbumin; "2" is Bovine serum albumin; "3" is Phosphorylase b; "4" is Beta-galactosidase; and "5" is Myosin.

EXAMPLE IV

Calibration Curve

As noted, SDS-PAGE protocols do not readily lend themselves to the production of calibration curves over a wide range of molecular weights. As should be appreciated, such curves can be utilized for, inter alia. the determination of the molecular weight of an unknown sample. Because the disclosed dynamically cross-linked composition can be used to efficiently separate low-to-high molecular weight proteins (i.e. 10,000 to 200,000 Daltons), such a calibration curve can be generated.

Figure 3:
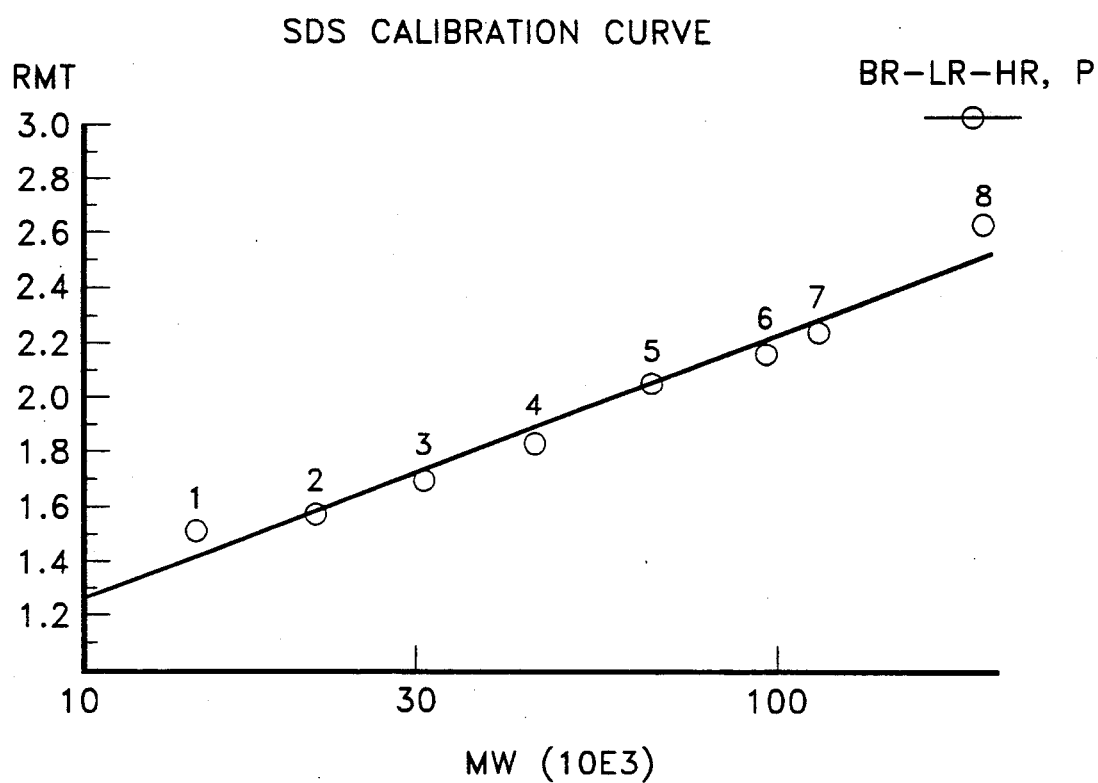
FIG. 3 is a calibration curve of the low-and high-molecular weight SDS-proteins of FIGS. 1 and 2 based upon the relative migration times thereof vis-a-vis an internal standard, Orange G.

FIG. 3 provides such a calibration curve, where each point represents the migration time of each SDS-protein complex relative to the internal standard. In FIG. 3, "1" is Lysozyme; "2" is Soybean trypsin inhibitor; "3" is Carbonic anhydrase; "4" is Ovalbumin; "5" is Bovine serum albumin; "6" is Phosphorylase b; "7" is Beta-galactosidase; and "8" is Myosin. The Relative Standard Deviation (RSD) for the calibration curve of FIG. 3 is 0.98.

Such a calibration curve has a myriad of applicable uses, including, but not limited to, determination of unknown protein molecular weights, and comparative analysis between natural-proteins and proteins derived via recombinant DNA technologies.

While the foregoing capillary column containing the dynamically cross-linked composition and method of use thereof has been described in considerable detail, it is to be understood that the invention is not limited to preferred or disclosed embodiments. The invention is not to be construed as limited in its applicability to the particular high performance capillary electrophoretic system described. Modifications and changes that are within the purview of those skilled in the art are intended to fall within the scope of the following claims.

What is claimed is:

1. A capillary column containing a dynamically cross-linked composition comprising:
   a) a capillary column having an interior cavity defined by a wall with an inner surface;
   b) a dynamically cross-linked composition filling said interior cavity, said composition comprising:
      i) between about 0.1% and about 1.5% polyethylene oxide;
      ii) between about 0.0% and less than about 2.0% polyethylene glycol;
      iii) between about 0.0% and about 2.0% of a surfactant;
      iv) between about 0.0M and about 1.0M of a pH buffer; and
      v) between about 0.0% and about 99% of a polyol; where the pH of the composition is between about 2.0 and about 10.0 and the viscosity of the composition is less than about 4,000 centipoise.

2. The capillary column of claim 1 further comprising a layer of a coating material on said inner surface of said wall.

3. The capillary column of claim 1 wherein said capillary is constructed of a material selected from the group consisting of glass, alumina, beryllia, fused silica and TEFLON.

4. The capillary column of claim 1 wherein said capillary is constructed of fused silica.

5. The capillary column of claim 1 wherein the internal diameter of said capillary is between about 2 $\mu$m and about 2000 $\mu$m.

6. The capillary column of claim 1 wherein said composition comprises about 1.0% polyethylene oxide.

7. The capillary column of claim 1 wherein said composition comprises about 1.0% polyethylene glycol.

8. The capillary column of claim 1 wherein said surfactant is selected from the group consisting of sodium-dodecyl sulphate, decyl-sulphate, polyoxyethylene ethers, polyoxyethylenesorbitans, deoxycholate, cetyltrimethylammonium bromide and cetylpyridinium chloride.

9. The capillary column of claim 1 wherein said surfactant is sodium dodecyl sulphate.

10. The capillary column of claim 9 wherein said composition comprises about 0.1% sodium dodecyl sulphate.

11. The capillary column of claim 1 wherein said pH buffer is ultra-violet light transparent.

12. The capillary column of claim 1 wherein said pH buffer comprises zwitterionic buffers.

13. The capillary column of claim 1 wherein said pH buffer is selected from the group consisting of 2-(N-morpholine) ethanesulfonic acid, N-(2-acetamido) iminodiacetic acid, piperazine-N,N'-bis(2-ethanesulfonic acid, N (2-acetamido)-2-aminoethanesulfonic acid, (2-aminoethyl) trimethyl-ammonium chloride hydrochloride, N,N-bis(2-hydroxy-ethyl)-2-aminoethane sulfonic acid, N-2-hydroxy-ethylpiperazine-N'-2-ethanesulfonic acid, tris-hydroxymethyl amino methane, N-tris(hydroxyl-methyl)methylglycine, N,N-bis(2-hydroxyethyl)-glycine, 2-(N-cyclohexylamino) ethanesulfonic acid and mixtures of the foregoing.

14. The capillary column of claim 1 wherein said pH buffer is a TRIS-CHES buffer.

15. The capillary column of claim 14 wherein the molarity of said buffer is 100 mM.

16. The capillary column of claim 15 wherein the pH of said composition is between about 8.0 and about 9.0.

17. A capillary column containing a dynamically cross-linked composition comprising:
   a) a capillary column having an interior cavity defined by a wall with an inner surface;
   b) a dynamically cross-linked composition filling said interior cavity, said composition comprising:
      i) about 1.0% polyethylene oxide;
      ii) about 1.0% polyethylene glycol
      iii) about 0.1% sodium dodecyl sulfate;
      iv) about 100 mm TRIS-CHES buffer; and
      v) about 1.0% ethylene glycol;
   where the pH of the composition is between about 8.0 and about 9.0 and the viscosity of the composition is less than about 500 centipoise.

18. A method of performing capillary electrophoresis comprising:
   a) introducing an aliquot of a sample containing constituents to be separated into a capillary column comprising a dynamically cross-linked composition, the capillary column comprising:
      i) a capillary column having an interior cavity defined by a wall with an inner surface; and
      ii) a dynamically cross-linked composition filling said interior cavity, said composition comprising:
         (a) between about 0.1% and about 1.5% polyethylene oxide;
         (b) between about 0.0% and less than about 2.0% polyethylene glycol;
         (c) between about 0.0% and about 2.0% of a surfactant;
         (d) between about 0.0M and about 1.0M of a pH buffer; and
         (e) between about 0.0% and about 99% of a polyol; where the pH of the composition is between about 2.0 and about 10.00 and the viscosity of the composition is less than about 4,000 centipoise;
   b) applying an electric field of at least about 10 volts per centimeter to the capillary column;
   c) separating the sample into its constituent parts; and
   d) detecting the constituents of the sample.

19. The method of claim 18 wherein said sample comprises surfactant-protein complexes.

20. The method of claim 19 wherein said surfactant of said surfactant-protein complexes is selected from the group consisting of sodium-dodecyl sulphate, decyl sulphate, polyoxyethylene ethers, polyoxyethylenesorbitans, deoxycholate, cetyltrimethylammonium bromide and cetylpyridinium chloride.

21. The method of claim 18 wherein said sample comprises sodium dodecyl sulphate-protein complexes.

22. The method of claim 18 wherein said detecting is selected from the group consisting of UV spectrophotometry, radioactive detecting of fluorescence detecting.

23. The method of claim 19 wherein said detecting is UV spectrophotometry at UV wavelengths in the range of 195–350 nm.

24. The method of claim 18 further comprising a layer of a coating material on said inner surface of said wall.

25. The method of claim 18 wherein said capillary is constructed of a material selected from the group consisting of glass, alumina, beryllia, fused silica and TEFLON.

26. The method of claim 18 wherein said capillary is constructed of fused silica.

27. The method of claim 18 wherein the internal diameter of said capillary is between about 2 μm and about 2000 μm.

28. The method of claim 18 wherein said composition comprises about 1.0% polyethylene oxide.

29. The method of claim 18 wherein said composition comprises about 1.0% polyethylene glycol.

30. The method of claim 18 wherein said surfactant is selected from the group consisting of sodium-dodecyl sulphate, decyl-sulphate, polyoxyethylene ethers, polyoxyethylenesorbitans, deoxycholate, cetyltrimethylammonium bromide and cetylpyridinium chloride.

31. The method of claim 18 wherein said surfactant is sodium dodecyl sulphate.

32. The method of claim 18 wherein said composition comprises about 0.1% sodium dodecyl sulphate.

33. The method of claim 18 wherein said pH buffer is ultra-violet light transparent.

34. The method of claim 18 wherein said pH buffer comprises zwitterionic buffers.

35. The method of claim 18 wherein said pH buffer is selected from the group consisting of 2-(N-morpholine) ethanesulfonic acid, N-(2-acetamido) iminodiacetic acid, piperazine-N,N'-bis(2-ethanesulfonic acid, N-(2-acetamido)-2-aminoethanesulfonic acid, (2-aminoethyl) trimethyl-ammonium chloride hydrochloride, N,N-bis(2-hydroxy-ethyl)-2-aminoethane sulfonic acid, N-2-hydroxyethylpiperazine-N'-2-ethanesulfonic acid, trishydroxymethyl amino methane, N-tris(hydroxylmethyl)methylglycine, N,N-bis(2-hydroxyethyl)-glycine, 2-(N-cyclohexylamino) ethane-sulfonic acid and mixtures of the foregoing.

36. The method of claim 18 wherein said pH buffer is a TRIS-CHES buffer.

37. The method of claim 36 wherein the molarity of said buffer is 100 mM.

38. The method of claim 18 wherein the pH of said composition is between about 8.0 and about 9.0.

39. A method of performing capillary electrophoresis on samples comprising sodium-dodecyl sulphate-protein complexes comprising
 a) introducing an aliquot of a sample comprising sodium-dodecyl sulphate-protein complexes into a capillary column comprising a dynamically cross-linked composition, the capillary column comprising
  i) a capillary column having an interior cavity defined by a wall with an inner surface, and
  ii) a dynamically cross-linked composition filling said interior cavity, said composition comprising
   (a) about 1.0% polyethylene oxide;
   (b) about 1.0% polyethylene glycol;
   (c) about 0.1% sodium dodecyl sulphate;
   (d) about 100 mM TRIS-CHES buffer; and
   (e) about 1.0% ethylene oxide:
 where the pH of the composition is between about 8.0 and about 9.0 and the viscosity of the composition is less than about 500 centipoise;
 b) applying an electrofield of at least about 10 volts per centimeter to the capillary column;
 c) separating the complexes; and
 d) detecting the complexes.

* * * * *